United States Patent
Oliver et al.

(10) Patent No.: US 10,184,906 B2
(45) Date of Patent: Jan. 22, 2019

(54) IDENTIFICATION, QUANTIFICATION AND PREDICTION OF FREE SILICON IN GEOLOGICAL FORMATION AND ITS CONTRIBUTION TO ROCK PROPERTIES

(71) Applicant: CGG SERVICES SAS, Massy (FR)

(72) Inventors: Guy Oliver, Katy, TX (US); Graham Spence, Conwy (GB); Chi Vinh Ly, Katy, TX (US); Fabien Allo, Rio De Janeiro (BR)

(73) Assignee: CGG SERVICES SAS, Massy (FR)

( * ) Notice: Subject to any disclaimer, the term of this patent is extended or adjusted under 35 U.S.C. 154(b) by 0 days.

(21) Appl. No.: 15/559,490

(22) PCT Filed: May 4, 2016

(86) PCT No.: PCT/IB2016/000851
§ 371 (c)(1),
(2) Date: Sep. 19, 2017

(87) PCT Pub. No.: WO2016/178094
PCT Pub. Date: Nov. 10, 2016

(65) Prior Publication Data
US 2018/0113086 A1    Apr. 26, 2018

Related U.S. Application Data

(60) Provisional application No. 62/208,844, filed on Aug. 24, 2015, provisional application No. 62/157,543, filed on May 6, 2015.

(51) Int. Cl.
*G01N 23/22*    (2018.01)
*E21B 43/30*    (2006.01)
(Continued)

(52) U.S. Cl.
CPC ....... *G01N 23/225* (2013.01); *E21B 41/0092* (2013.01); *E21B 43/30* (2013.01);
(Continued)

(58) Field of Classification Search
CPC .. G01N 23/223; G01N 23/2251; E21B 49/00; E21B 49/005; G01V 99/005
See application file for complete search history.

(56) References Cited

U.S. PATENT DOCUMENTS

2013/0270011 A1    10/2013  Akkurt et al.
2014/0377872 A1*  12/2014  Brosse ............... G01V 11/00
                                                                       436/29
(Continued)

FOREIGN PATENT DOCUMENTS

EP    2 816 377 A1    12/2014
WO    2013/144458 A1    10/2013

OTHER PUBLICATIONS

International Search Report, and Written Opinion, dated Aug. 29, 2016, from corresponding PCT application No. PCT/IB2016/000851.

*Primary Examiner* — Michael C Bryant
(74) *Attorney, Agent, or Firm* — Patent Portfolio Builders PLLC

(57) ABSTRACT

Predicting and quantifying free silicon in a geological formation generates free silicon data for a physical sample obtained from within the geological formation. The free silicon data include identification of portions of the physical sample containing free silicon and a quantification of the free silicon contained in the portions of the physical sample containing free silicon. A modified petro-elastic model for the geological formation comprising rock constituents is generated that incorporates free silicon as one of the rock constituents and that quantitatively models how free silicon changes elastic properties within the geological formation. A
(Continued)

three-dimensional model of the geological formation is created that indicates volumes of free silicon throughout the geological formation. The three-dimensional model is created using geophysical data obtained from the physical sample, seismic data covering the geological formation and the modified petro-elastic model.

20 Claims, 3 Drawing Sheets

(51) Int. Cl.
    *E21B 49/00*     (2006.01)
    *G01V 99/00*     (2009.01)
    *G01N 23/225*     (2018.01)
    *G01N 33/24*     (2006.01)
    *E21B 41/00*     (2006.01)
    *E21B 49/02*     (2006.01)
    *E21B 25/00*     (2006.01)

(52) U.S. Cl.
    CPC ............. *E21B 49/02* (2013.01); *G01N 33/24* (2013.01); *G01V 99/005* (2013.01); *E21B 25/00* (2013.01)

(56) References Cited

U.S. PATENT DOCUMENTS

| | | |
|---|---|---|
| 2015/0000903 A1 | 1/2015 | Ly et al. |
| 2015/0025863 A1 | 1/2015 | Walls et al. |
| 2015/0095001 A1 | 4/2015 | Massonnat |
| 2018/0031732 A1* | 2/2018 | Mosse ................... G01V 1/50 |

* cited by examiner

IDENTIFICATION, QUANTIFICATION AND PREDICTION OF FREE SILICON IN GEOLOGICAL FORMATION AND ITS CONTRIBUTION TO ROCK PROPERTIES

CROSS REFERENCE TO RELATED APPLICATIONS

The present application is a National Stage of PCT Application No. PCT/IB2016/000851, filed May 4, 2016, which claims priority and benefit from U.S. Provisional Patent Application Nos. 62/157,543, filed May 6, 2015, for "Identification, Quantification And Prediction Of Free Silicon In Geological Formation And Its Contribution To Rock Properties" and 62/208,844, filed Aug. 24, 2015, for "Identification, Quantification And Prediction Of Free Silicon In Geological Formation And Its Contribution To Rock Properties", the entire contents of which are incorporated herein by reference.

TECHNICAL FIELD

Embodiments of the subject matter disclosed herein generally relate to methods and systems for hydrocarbon, gas and petroleum production from wells using fracturing techniques.

BACKGROUND

Hydraulic fracturing, which is also known as fracking, involves the high-pressure injection of fluid into a well passing through a given subsurface in which oil, gas and petroleum reservoirs are located in order to create cracks in the rock formations through which fluids including the oil, natural gas and petroleum can flow more freely. In general, the target reservoirs are typically porous sandstones, limestones or dolomite rocks. However these reservoirs also include what is termed unconventional reservoirs that include shale rock or coal beds. Also included in the subsurface are clays and kerogen filled pores in unconventional reservoirs. The effectiveness of hydraulic fracturing in a given subsurface depends on factors including the mineralogy of that subsurface and the presence of free silicon.

Free silicon is sourced by the dissolution of planktonic organisms, from residual silicon from pore fluids or from silicon released during weathering. It is amorphous and not mineralized into silicon dioxide crystals. The presence of free silicon within siliciclastic and calcareous mudstones can create a rigid high modulus framework that has the potential to mitigate the adverse effects of high clay content with respect to drilling and completions and may ultimately lead to better hydraulic fracturing and improved production.

Current analytical techniques, however, do not fully quantify or correctly interpret free silicon phases within certain lithologies, because the silicon may not be a mineralized species. The free silicon can be either an amorphous silicon dioxide phase or silicon ions locked within interstitial crystal lattice spaces. These forms of silicon prove to be difficult to determine using classical techniques such as traditional X-ray diffraction (XRD) and X-ray fluorescence (XRF), which are based on the fact that the matter to analyze is in a crystalized form.

In XRD, the analytical methodology measures the bond dimensions of crystal lattices. An incoming monochromatic polarized X-ray beam irradiates a sample surface, interacts with atoms located in different crystal layers and reflects back, away from the surface. Traditional scanning of a sample through different angles provides an XRD trace containing peaks corresponding to different angles that relate to constructive interference conditions from certain mineral species and certain lattice dimension. It is therefore possible to interpret which mineral species are present within the sample and ultimately to determine a quantitative estimate of their relative mass percent abundance.

However, in the case of free silicon, if the silicon occurs as an amorphous, i.e., poorly crystalline, silicon dioxide species. The lack of a crystal structure makes it very difficult for XRD to detect the presence of this material or to determine the amount of this material in the sample. The same problem occurs if the free silicon exists as inclusions locked within interstitial crystal spaces, as this silicon will not register on the XRD trace as a unique peak. These limitations of XRD analysis can result in overestimated quantities of highly crystalline materials, such as quartz, due to the underestimation of poorly to non-crystalline species, such as amorphous silicon and some clays.

Unlike XRD, XRF is used for the determination of the elemental composition of a sample, is not sensitive to the location of the elements in the sample and has a relatively good detection limit. XRF irradiates samples with a monochromatic X-ray beam and measures the resultant X-ray fluorescence induced by the incident beam. The induced fluorescence from the sample material is generated by the interaction between the incident X-ray beam and the various outer shell electrons that triggers the transition of an electron from a higher energy shell to fill the free space left by the ejected electron from the outer shell. This transition of a high energy electron toward a lower energy shell is coupled to the emission of an X-ray photon whose energy corresponds to the difference of energy between the two shells. The energy of the photon is therefore specific and allows identifying the type of atom present in the sample by analyzing peaks that represent a given element and the amplitude of those peaks, which indicate the amount of that element.

However, the base output data from XRF is the elemental composition of the sample, not its mineralogy. Methods to obtain the mineralogy using mass balance equations generally work when the lithology is well known and when dealing with a fully mineralized sample. However the mass balance process does not allow for "left-over" elements, meaning that any excess silicon in the sample such as free silicon, which cannot be assigned to complex silicates, ends up being assigned to quartz. As a result, in samples containing silicon as free ions in interstitial crystal spaces, the resultant bulk mineralogy will generally overestimate quartz due to this limitation, and leave the free-silicon unresolved.

SUMMARY

Exemplary embodiments are directed to systems and methods that combine elements of traditional analyses, such as XRF, with other techniques, such as scanning electron microscopy, to utilize the strengths of these analytical techniques to both detect and quantify the presence of free-silicon in geological samples. Once the free silicon phases have been identified and quantified in geological samples, a rock physics analysis at a given core or subsurface sample such as a wellbore is considered. Petro-elastic models (PEMs) link the rock properties, i.e., the content of free silicon, to the elastic attributes of the rock. Once calibrated at the well location, those PEMs can be used to drive a petrophysical seismic inversion and deliver an estimate of rock property of interest away from the location of the sample, e.g., the borehole. Since available unconsolidated or consolidated sand or shale models do not properly model the high modulus framework, a new petro-elastic model is created to better reflect the increased rigidity that free silicon brings to the rock. Once free silicon has been identified, measured and correctly integrated into a calibrated petro-elastic model, the presence or absence of free silicon away from the borehole is predicted using at least one of well log data, seismic data and the new or modified petro-elastic model. This presence or absence of free silicon can be used to determine locations for wells in the geological formation.

An exemplary embodiment is directed to a method for predicting and quantifying free silicon in a geological formation. Free silicon data are generated for a physical sample obtained from within the geological formation. The free silicon data include an identification of portions of the physical sample containing free silicon and a quantification of the free silicon contained in the portions of the physical sample containing free silicon. A modified petro-elastic model is generated for the geological formation that includes rock constituents that incorporates free silicon as one of the rock constituents. The modified petro-elastic model quantitatively models how free silicon changes elastic properties within the geological formation. Therefore, the modified petro-elastic model is used, for example, to determine locations for wells in the geological formation. For example, a three-dimensional model of the geological formation is created that indicates volumes of free silicon throughout the geological formation using geophysical data obtained from the physical sample, seismic data covering the geological formation and the modified petro-elastic model.

In one embodiment, generating the free silicon data further includes using scanning electron microscope-energy dispersive spectrometry on portions of the physical sample to generate the identification of portions of the physical sample containing free silicon. Using scanning electron microscope-energy dispersive spectrometry includes using at least one of leptonic beam scanning and baryonic beam scanning. In one embodiment, using scanning electron microscope-energy dispersive spectrometry includes quantifying at least one of a ratio of silicon to aluminum, a ratio of zirconium to aluminum and an amount of molybdenum in each one of the portions of the physical sample. In one embodiment, using scanning electron microscope-energy dispersive spectrometry includes identifying portions of the physical sample having an increase in a ratio of silicon to aluminum. Generating the free silicon data includes using high magnification scanning electron microscopy on the portions of the physical sample containing free silicon to generate the quantification of the free silicon contained in the portions of the physical sample containing free silicon.

In one embodiment, the physical sample obtained from within the geological formation includes at least one of a vertical borehole core and a horizontal borehole core. The portions of the physical sample represent intervals along the vertical borehole core or horizontal borehole core corresponding to horizontal zones or vertical zones within the geological formation. In one embodiment, generating a modified petro-elastic model includes generating at least one of a modified mineral elastic properties model and a modified dry rock elastic properties model. In one embodiment, creating the three-dimensional model of the geological formation further includes performing a petrophysical inversion using the modified petro-elastic model to create the three-dimensional model of the geological formation containing an estimation of volumes of free silicon within the geological formation.

In one embodiment, creating the three-dimensional model of the geological formation includes at least one of performing an elastic stochastic inversion to generate a plurality of elastic models and performing a petrophysical stochastic inversion to generate a plurality of petrophysical models to determine an uncertainty in the volumes of free silicon in the three-dimensional model of the geological formation. In one embodiment, the method further includes using the three-dimensional model of the geological formation indicating volumes of free silicon throughout the geological formation to determine locations for wells in the geological formation.

Exemplary embodiments are also directed to a computer-readable medium containing computer-executable code that when read by a computer causes the computer to perform a method for predicting and quantifying free silicon in a geological formation. This method includes generating free silicon data for a physical sample obtained from within the geological formation where the free silicon data include an identification of portions of the physical sample containing free silicon and a quantification of the free silicon contained in the portions of the physical sample containing free silicon, generating a modified petro-elastic model for the geological formation comprising rock constituents that incorporates free silicon as one of the rock constituents and that quantitatively models how free silicon changes elastic properties within the geological formation and using the modified petro-elastic model is used to determine locations for wells in the geological formation. For example, a three-dimensional model of the geological formation is created that indicates volumes of free silicon throughout the geological formation using geophysical data obtained from the physical sample, seismic data covering the geological formation and the modified petro-elastic model.

An exemplary embodiment is directed to a computing system for predicting and quantifying free silicon in a geological formation. The computing system includes a storage device containing geophysical data obtained from a physical sample obtained from within the geological formation and seismic data covering the geological formation. The computing system also includes a processer in communication with the storage device. The processor is configured to generate free silicon data for the physical sample where the free silicon data includes an identification of portions of the physical sample containing free silicon and a quantification of the free silicon contained in the portions of the physical sample containing free silicon, to generate a modified petro-elastic model for the geological formation containing rock constituents that incorporates free silicon as one of the rock constituents and that quantitatively models how free silicon changes elastic properties within the geological formation and to use the modified petro-elastic model is used, to determine locations for wells in the geological formation. For example, the processor is configured to create a three-dimensional model of the geological formation indicating volumes of free silicon throughout the geological formation using the geophysical data obtained from the physical sample, the seismic data covering the geological formation and the modified petro-elastic model.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the embodiments refers to the accompanying drawings. The same reference numbers in different drawings identify the same or similar elements. The following detailed description does not limit the invention. Instead, the scope of the invention is defined by the appended claims. Some of the following embodiments are discussed, for simplicity, with regard to local activity taking place within the area of a seismic survey. However, the embodiments to be discussed next are not limited to this configuration, but may be extended to other arrangements that include regional activity, conventional seismic surveys, etc.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Exemplary embodiments of systems and methods predict the effectiveness of hydraulic fracturing and the ultimate recovery of hydrocarbons from reservoirs in a given project area, i.e., a given geological formation. As used herein, the project area refers to a physical area that can cover, for example, one or more counties in a state. The subsurface below the project area contains at least one and possibly a plurality of oil, natural gas or petroleum reservoirs, both conventional reservoirs and unconventional reservoirs. These reservoirs can be located at different intervals, i.e., spanning through different depths, in the subsurface. For a given project area, there is a consistency in core data obtained from wells passing through the subsurface.

Figure 1:
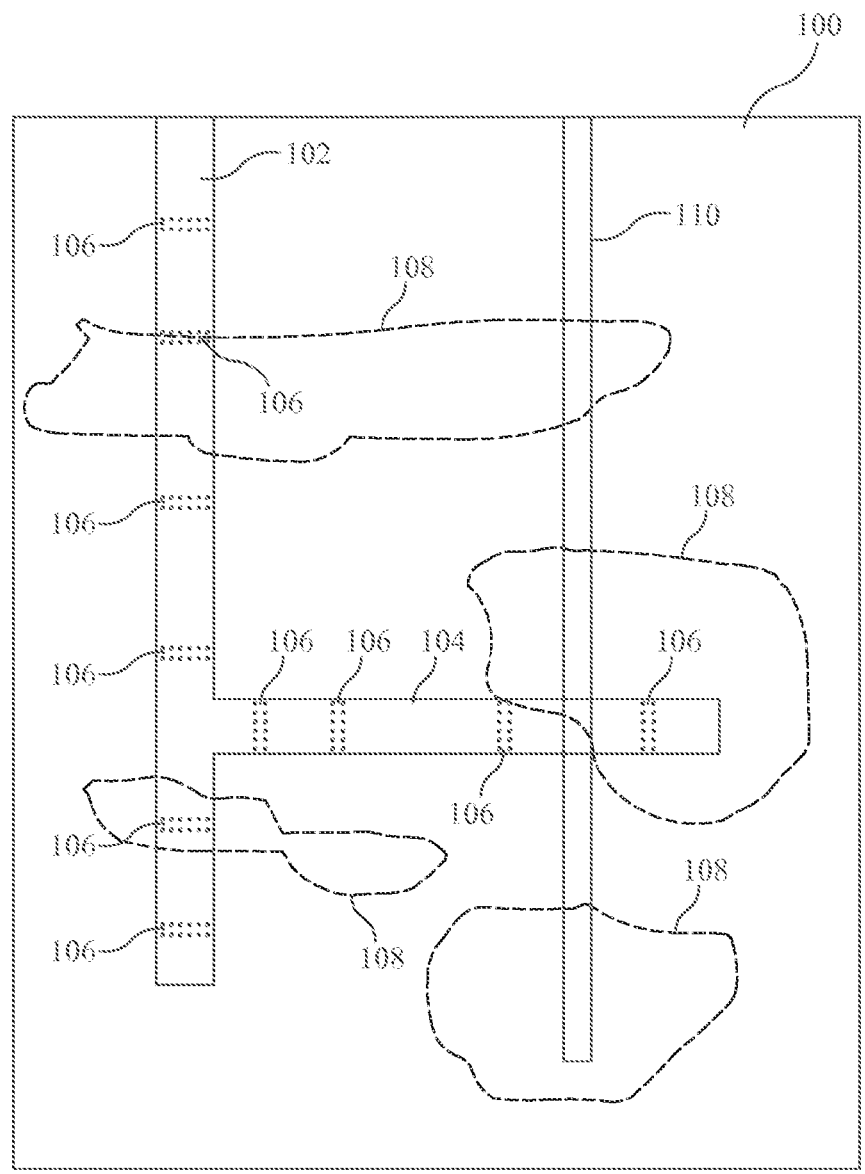
FIG. 1 is a schematic representation of a geological formation showing borehole samples and volumes of free silicon.

Referring initially to FIG. 1, exemplary embodiments of systems and methods provide for the identification and quantification of volumes of free silicon 108 within a given geological formation. While illustrated in two-dimensions, the volumes of free silicon are identified and quantified in three-dimensions such as a three-dimensional cube of the geological formation. This three-dimensional representation of the volumes of free silicon is used to locate future wells 110 within the geological formation in particular in areas of the subsurface containing the volumes of free silicon. This will optimize the effectiveness of hydraulic fracture treatment and reservoir productivity in the geological formation 100.

The volumes of free silicon are determined using data obtained from a plurality of portions 106 of physical samples obtained from the geological formation. Any suitable methods known and available in the art for obtaining physical samples of a geological formation or subsurface area of interest can be used. In one embodiment, the physical samples are borehole cores from at least one of vertical boreholes 102 and horizontal boreholes 104 passing though the geological formation. The plurality of portions are slices or cuttings from the borehole cores, e.g., by facies, over the intervals of interest within the geological formation. Therefore, each one of the plurality of portions of the physical samples correspond to horizontal zones or strata or vertical zones or strata within the geological formation.

A two-step process is used to determine the amount of free silicon in each one of the plurality of portions of the physical sample. The two-step process utilizes Scanning Electron Microscope-Energy Dispersive Spectrometry (SEM-EDS) to identify the portions of the physical sample containing free silicon followed by high magnification scanning electron microscopy to quantify an amount of free silicon in those portions determined to contain free silicon. As used herein, SEM-EDS is the use of a leptonic beam to scan a samples surface, and the use of induced EM radiation from the interaction of the leptonic beam and the sample surface to determine the elemental composition at each scanned point. In one embodiment, the identification and quantification of free silicon is performed using the RoqSCAN™ wellsite mineralogical analyzer, which is commercially available from Baker Hughes Incorporated of Houston, Tex.; however, other types of analyzers can be used.

In one embodiment, one or more of leptonic beam scanning and baryonic beam scanning is used to determine the bulk elemental composition of the geological sample. This will quantify, for example, the ratio of silicon to aluminum (Si/Al), the ratio of zirconium to aluminum (Zr/Al) and the amount of Molybdenum (Mo) in each portion, i.e., the identification of multi-silica phases. These ratios and amounts can then be used to determine which portions of the physical sample contain free silicon. For example, an increase in the Si/Al ratio of a given sample can indicate the presence of free silicon.

The portions of the physical sample identified as containing free silicon are then subjected to higher magnification scanning electron microscopy (SEM). High resolution SEM imaging includes using at least one of leptonic and baryonic beams. The images collected from the scanning beams from the resultant electron, leptonic or baryonic emissions are used to confirm and to quantify the distribution of the free silicon phases within the portions of the physical samples. In one embodiment, cathodoluminescence (CL) is used to analyze the portions of the physical sample identified as containing free silicon. The result is free silicon data for the physical sample of the geological formation. If desired, rock mechanical testing can be used to define the physical effect of different levels of free silicon within the geological formation. Rock mechanical testing can be used in determining the most desired locations for hydraulic fracturing based on the determined levels of free silicon.

Embodiments provide for the identification of volumes of free silicon throughout the geological formation. Therefore, data obtained from the physical samples, including the free silicon data, are extrapolated to areas of the geological formation outside the location of the physical samples, e.g., away from the boreholes. Knowing the free silicon data throughout the geological formation provide for a determination of locations of wells in the geological formation that can take advantage of the presence of free silicon. This extrapolation is provided using a rock physics or petro-elastic model for the geological formation. In particular, the free silicon data for the geological formation are incorporated into existing petro-elastic models to generate one or more modified petro-elastic models. Therefore, the modified petro-elastic models are used to determine locations for wells in the geological formation.

Having identified the fractions of free silicon in the geological formation, a petro-elastic model for the geological formation comprising rock constituents is generated. The petro-elastic model incorporates free silicon as one of the rock constituents and quantitatively models how free silicon changes elastic properties within the geological formation. In general, the fractions or volume fractions of the free silicon and the elastic properties of free silicon are incorporated into existing equations that provide for the determination of the elastic properties of a given volume, e.g., the geological formation, based on the constituents within that volume. These elastic properties include, for example, the bulk density, the bulk modulus and the shear modulus. In general, petro-elastic models (PEMs) are divided into three distinct parts, the definition of the effective mineral properties, the definition of the dry rock properties and the fluid substitution, to model the saturated rock properties. In one embodiment, the first two parts of the PEM are modified to take free silicon into account in the PEM.

The modeling of the mineral properties, e.g., density, bulk modulus and shear modulus, follows and utilizes one or more, i.e., a combination, of the following equations upgraded to include the free silicon. The Voigt upper bound model provides an upper bound on the effective elastic modulus of a given volume containing a mixture of a plurality, N, of different material phases. For example, the Voigt model, V, can express the effective elastic modulus, M, of a given volume as $M_v = \Sigma_{i=1}^{N} f_i M_i$, where $f_i$ is the volume fraction of any given material phase. Similarly, the Reuss lower bound model provides a lower bound on the effective elastic modulus of a given volume containing a mixture of a plurality, N, of different material phases. For example, the Reuss model, R, can express the effective elastic modulus, M, of a given volume as $$\frac{1}{M_R} = \sum_{i=1}^{N} \frac{f_i}{M_i},$$

again where $f_i$ is the volume fraction of any given material phase. The narrowest range of elastic moduli without incorporating any information regarding the geometry of the phases is given by the Hashin-Shtrikman bounds. For two constituents or phases, the Hashin-Shtrikman bulk moduli bounds are given by $$K_{HS\pm} = K_1 + \frac{f_2}{(K_2 - K_1)^{-1} + f_1\left(K_1 + \frac{4}{3}\mu_1\right)^{-1}}.$$

Similarly, the Hashin-Shtrikman shear moduli bounds are given by $$\mu_{HS\pm} = \mu_1 + \frac{f_2}{(\mu_2 - \mu_1)^{-1} + \frac{2f_1(K_1 + 2\mu_1)}{5\mu_1\left(K_1 + \frac{4}{3}\mu_1\right)}}.$$

The upper and lower bounds are computed by interchanging which constituent is termed 1 and which is termed 2. As used in these equations, $K_i$ is the bulk modulus of the $i^{th}$ constituent of phase, $\mu_i$ is the shear modulus of the $i^{th}$ constituent of phase and $f_i$ is the volume fraction of the $i^{th}$ constituent of phase. The volume fraction of free silicon can be directly introduced in the previous equations as one of the mineral volume fractions to estimate the elastic properties of the effective mineral content of the rock including free silicon.

Modeling the dry rock properties, e.g., dry rock bulk modulus and shear modulus, is more complex than modeling the effective mineral phase properties as this is dependent on the geometry of the pore space and the contacts between the different minerals. There is therefore a great variety of available models depending on the rock type. Any method to model dry rock elastic properties that is known and available in the art can be used. In one embodiment, grain-based models (based on Hertz-Mindlin model) and inclusion-based models (based on Kuster-Toksöz model) are used. According to the Hertz-Mindlin model, the dry rock bulk modulus is given by $$K_{dry} = \left[\frac{C^2(1-\phi)^2\mu^2}{18\pi^2(1-\nu)^2}P\right]^{1/3}$$

and the dry rock shear modulus is given by $$G_{dry} = \frac{5-4\nu}{5(2-\nu)}\left[\frac{3C^2(1-\phi)^2\mu^2}{2\pi^2(1-\nu)^2}P\right]^{1/3}$$

where P is the effective pressure the rock is subjected to, $\phi$ is the rock porosity, C is the number of contacts between grains (also known as coordination number) and $\nu$ and $\mu$ are the Poisson ratio and shear modulus of the solid grains respectively. In this particular case, the coordination number can be adjusted to take into account the presence of free silicon in the geological formation. The modified model provides an estimate of the elastic properties of the geological formation that incorporate the free silicon data obtained from the sample of the geological formation.

The modified petro-elastic model, for example in combination with additional data, can be used to generate a three-dimensional representation of the free silicon within the geological formation. These additional data include geophysical data obtained from the physical sample and seismic data covering the geological formation. The geophysical data include a basic suite of well log data, for example, well log data continuously obtained from a wireline is available for all of the wells in the project area. This basic suite of well log data includes neutron porosity, gamma ray measurement, resistivity and litho-density (photo-electric factor (PEF) and density). In one embodiment, the geophysical data include core data. Core data represent discrete measurements obtained, for example, from laboratory measurements of well cores, including full-bore cores and rotary side-wall cores, obtained from the well. The core data include mineralogy, porosity and permeability. The geological data can also include dipole sonic data (p-wave sonic data and s-wave sonic data). In one embodiment, the additional data include existing geological studies.

The seismic data include, for example, data obtained using any type of seismic survey known and available in the art. In one embodiment, the seismic data include three-dimensional angle stacks with associated representative one-dimensional wavelets. In one embodiment, the seismic data can be used to generate elastic data or elastic properties of the geological formation, for example, using seismic data in combination with inversion techniques. Suitable inversion techniques to extract elastic properties from seismic data are known and available in the art. In one embodiment, the result of seismic inversion provides, for example, three-dimensional cubes of $V_p$, $V_s$ and density and derived attributes such as $I_p$, $I_s$ and $V_p/V_s$.

The available data and models, i.e., the geophysical data obtained from the physical sample, seismic data covering the geological formation and the modified petro-elastic models are used to classify the geological layers within the geological formation in terms of free silicon content. This facies classification based on geophysical data or log data, seismic inversion results (elastic attributes) and the new petro-elastic models is used to create the three-dimensional model or cube indicating the presence of free silicon in the geological formation away from the location of the sample, e.g., away from the borehole.

In one embodiment, a petrophysical inversion or an inverse rock physics transform based on the new petro-elastic model is used to estimate the volume of free silicon within the geological formation based on the assumption that all other properties like porosity, pressure, saturations, and mineral volumes are known. Alternatively, a stochastic inversion, either elastic or petrophysical, is used to generate multiple elastic or petrophysical models of the geological formation to investigate the uncertainty regarding the free silicon content away from the sample site, i.e., the borehole.

Having created the three-dimensional model of the geological formation indicating the existence and location of free silicon within the geological formation, this model can be saved or output and displayed to a user. The displayed three-dimensional model can be used in the determination and location of future wells that are drilled within the geological formation in order to take advantage of the free silicon to improve hydraulic fracturing operations for reservoir production.

Figure 2:
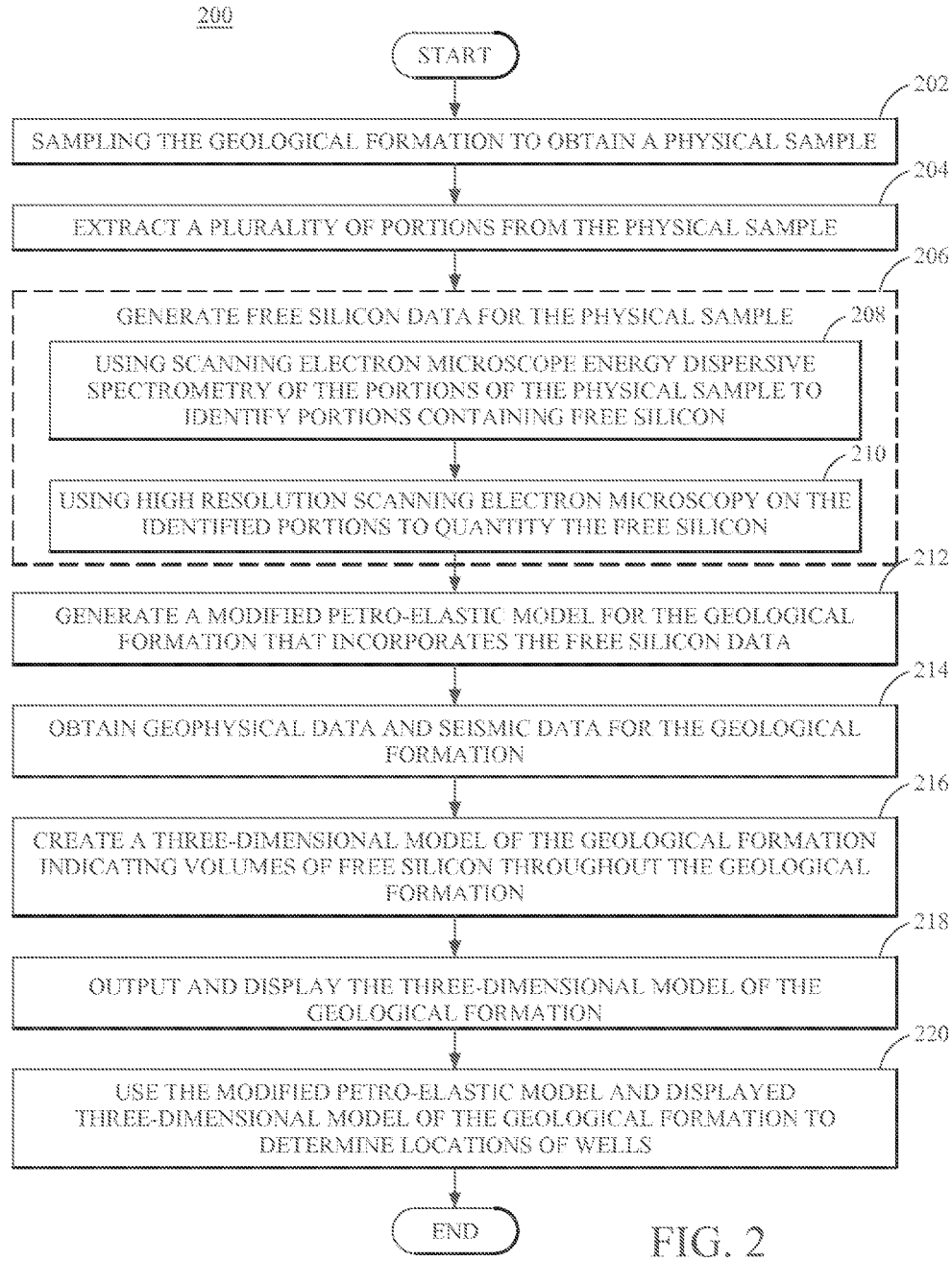
FIG. 2 is a flowchart of an embodiment of a method for predicting and quantifying free silicon in a geological formation.

Referring to FIG. 2, an exemplary embodiment of a method for predicting and quantifying free silicon in a geological formation 200 is illustrated. The geological formation is sampled to obtain at least one physical sample of the geological formation 202. Any suitable method for physically sampling a geological formation or subsurface region that is known and available in the art can be used. In one embodiment, each sample is a core obtained from a borehole drilled through the geological formation. The boreholes can be drilled vertically, horizontally or at an angle offset from vertical and horizontal through the geological formation. Therefore, suitable borehole cores include, but are not limited to at least one of a vertical borehole core and a horizontal borehole core. A given physical sample of the geological formation extends through multiple vertical or horizontal facies, zones or strata in the geological formation.

A plurality of portions is extracted from each physical sample of the geological formation 204. In one embodiment, a given extracted portion from the plurality of portions corresponds to a given vertical or horizontal facies, zone or strata within the geological formation. Any suitable methods for extracting portions from geological samples known and available in the art can be used. In one embodiment, each portion is a slice through a given location along a borehole core. These locations correspond to horizontal zones or vertical zones within the geological formation. Alternatively, a plurality of plugs or cylinders is extracted along the length of a borehole core and each portion is a slice through the extracted bore plugs.

Having obtained one or more physical samples and the plurality of portions of each physical sample, free silicon data are generate for each physical sample obtained from within the geological formation 206. The free silicon data include an identification of portions of the physical sample containing free silicon and a quantification of the free silicon contained in the portions of the physical sample containing free silicon. The generation of the free silicon data includes using scanning electron microscope-energy dispersive spectrometry of the portions of the physical sample to generate the identification of portions of the physical sample containing free silicon 208. This is followed by using high magnification scanning electron microscopy on the portions of the physical sample containing free silicon to generate the quantification of the free silicon contained in the portions of the physical sample containing free silicon 210.

In one embodiment, leptonic or baryonic beam scanning is used to determine the bulk mineral composition of the sample. In addition this analysis further quantifies at least one of a ratio of silicon to aluminum, a ratio of zirconium to aluminum and an amount of molybdenum in each one of the portions of the physical sample. These ratios are used to identify multiple silicon phases within the portions of the physical sample. For example, portions of the physical sample having an increase in a ratio of silicon to aluminum are identified as including free silicon.

At least one modified petro-elastic model for the geological formation is generated that incorporates the effect of the generated free silicon data 212 on the elastic properties of the rocks within the geological formation. This includes a modified mineral elastic properties calculation and a modified dry rock elastic properties calculation. Additional geophysical data are obtained from the physical sample and seismic data covering the geological formation 214. The seismic data can be used to generate elastic data for the geological formation using, for example, inversion techniques.

A three-dimensional model of the geological formation indicating volumes of free silicon throughout the geological formation is generated 216. This three-dimensional model is generated using geophysical data obtained from the physical sample, seismic data covering the geological formation and the modified petro-elastic model.

In one embodiment, a petrophysical inversion using the modified petro-elastic model is used to create the three-dimensional model of the geological formation. This three-dimensional model includes an estimation of volumes of free silicon within the geological formation. In another embodiment, at least one of performing an elastic stochastic inversion to generate a plurality of elastic models and performing a petrophysical stochastic inversion is used to generate a plurality of petrophysical models. These models are used to determine an uncertainty in the volumes of free silicon in the three-dimensional model of the geological formation.

The generated three-dimensional model of the geological formation is then outputted and displayed to a user 218. The three-dimensional model can also be saved for future reference and comparison. At least one of the modified petro-elastic model and the displayed three-dimensional model of the geological formation indicating volumes of free silicon throughout the geological formation is used to determine locations for wells, i.e., future wells or new wells to be drilled, in the geological formation 220. These new wells are located to take advantage of and pass through regions of the geological formation containing free silicon in order to improve the effectiveness of hydraulic fracturing and production from reservoirs within the geological formation.

Exemplary embodiments, in identifying and quantifying free silicon in samples obtained from the geophysical formation, combine elements of traditional analyses, such as XRF, with other techniques, such as scanning electron microscopy. The workflow makes use of the strengths of these analytical techniques to both detect and quantify the presence of free silicon in geological samples.

Once the free silicon phases have been identified and quantified in the physical samples of the geological formation, a rock physics analysis at the location of the physical samples, e.g., the wellbore, is considered. Petro-elastic models (PEMs) link the rock properties, e.g., the content of free silicon, to the elastic attributes of the rock. Once calibrated at the physical sample location, those PEMs are used to drive a petrophysical seismic inversion and deliver an estimate of the rock property of interest away from the borehole. A new petro-elastic model is created to reflect more accurately the increased rigidity that free silicon brings to the rock.

Once the free silicon has been identified, measured and correctly integrated into a calibrated petro-elastic model, the presence or absence of free silicon is predicted away from the sample location based on seismic data and the new petro-elastic model. Exemplary embodiments provide for the identification and quantification of intervals of increased free silicon, i.e., rigid high modulus zones, in the vertical and lateral boreholes, leading to improved completion modelling. An improved understanding of formation rheology strengthens geomechanical models, particularly where data are sparse. The predicted three-dimensional cubes indicating the presence of free silicon away from the borehole assist with future well planning and spacing.

Exemplary methods are integrated with measured textural data, e.g., porosity, pore size distribution and pore aspect ratio, to enable the generation of a more geologically constrained elastic properties model. This modelling is then used to model completion conditions of theoretical wells before they are drilled, as well as also assisting in designing completions of wells in the process of being drilled and finally designing completions for those wells that have been completed and are candidates for re-completion.

Additionally, exemplary embodiments are used to determine the presence of other free ions in a geological setting. Adjustments to the petro-elastic models are then made to account for these additional free elemental ions, depending on their impact on the elastic rock properties. This allows exemplary methods to be applied to both unconventional and complex oil and gas reservoirs as well as other natural resource reservoirs.

Figure 3:
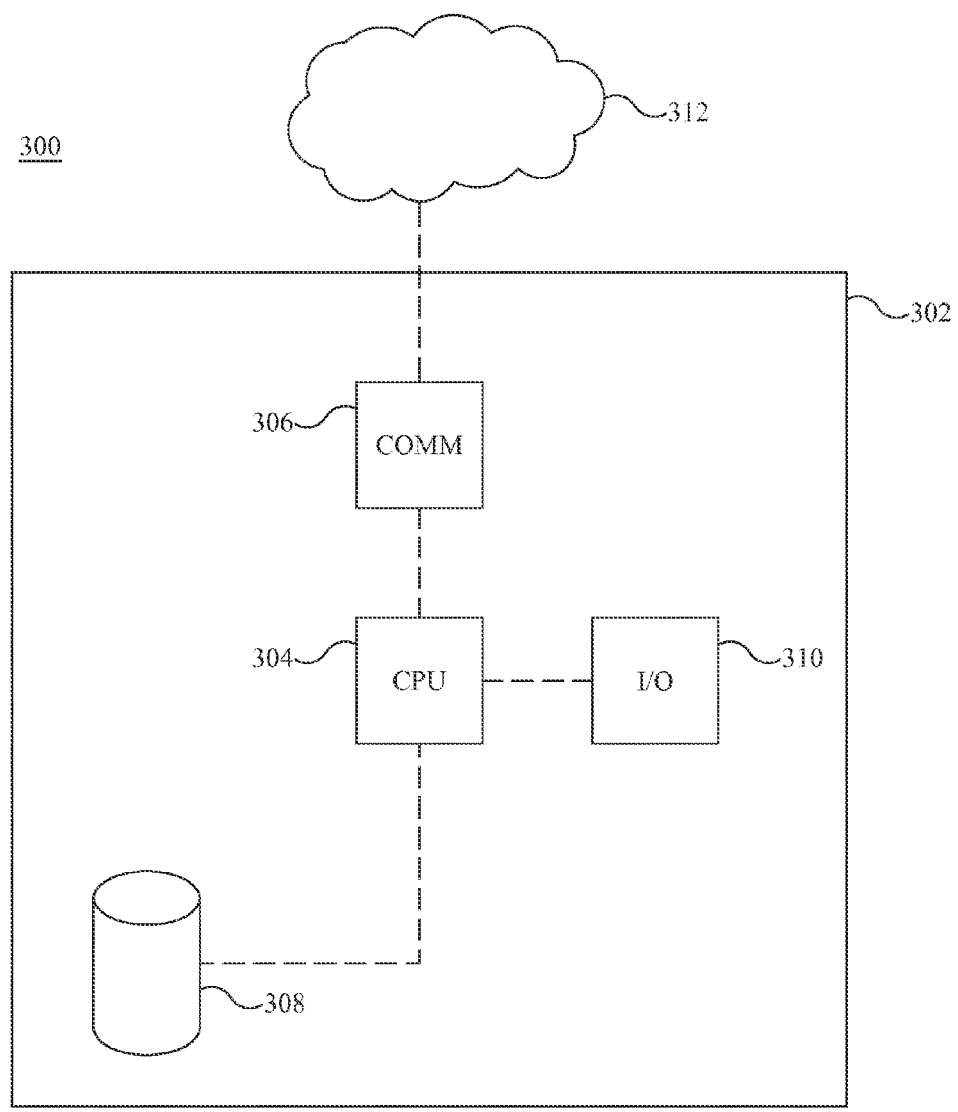
FIG. 3 is a schematic representation of an embodiment of a computing system for use in executing method for predicting and quantifying free silicon in a geological formation.

Referring now to FIG. 3, exemplary embodiments are directed to a computing system 300 for predicting and quantifying free silicon in a geological formation. In one embodiment, a computing device is used to perform the calculations as set forth in the above-described embodiments. Suitable computing devices may be any type of computing device capable of obtaining, processing and communicating multi-vintage seismic data associated with seismic surveys conducted at different time periods. The computing system 300 includes a computer or server 302 having one or more central processing units 304 in communication with a communication module 306, one or more input/output devices 310 and at least one storage device 308.

The communication module is used to obtain well log data, core data and dipole sonic data for a plurality of wells passing through a subsurface region in a project area, e.g., a geological formation, as well as seismic data covering the geological formation. These well log data, core data and dipole sonic data can be obtained, for example, through the input/output devices. The well log data, core data and dipole sonic data are stored in the storage device. In addition, the storage device is used to store geophysical data obtained from a physical sample obtained from within the geological formation and seismic data covering the geological formation. The input/output device can also be used to communicate or to display the model of free silicon in the geological formation, for example, to a user of the computing system.

The processor is in communication with the communication module and storage device and is configured to generate free silicon data for the physical sample, where the free silicon data include an identification of portions of the physical sample containing free silicon and a quantification of the free silicon contained in the portions of the physical sample containing free silicon. The processor is further configured to generate a modified petro-elastic model for the geological formation that incorporates the free silicon data and to create a three-dimensional model of the geological formation indicating volumes of free silicon throughout the geological formation using the geophysical data obtained from the physical sample, the seismic data covering the geological formation and the modified petro-elastic model. In general, the processor is configured to perform any of the functions including the computational functions of method for predicting and quantifying free silicon in a geological formation as discussed herein.

Suitable embodiments for the various components of the computing system are known to those of ordinary skill in the art, and this description includes all known and future variants of these types of devices. The communication module provides for communication with other computing systems, databases and data acquisition systems across one or more local or wide area networks 312. This includes both wired and wireless communication. Suitable input/output devices include keyboards, point and click type devices, audio devices, optical media devices and visual displays.

Suitable storage devices include magnetic media such as a hard disk drive (HDD), solid state memory devices including flash drives, ROM and RAM and optical media. The storage device can contain data as well as software code for executing the functions of the computing system and the functions in accordance with the methods described herein. Therefore, the computing system 300 can be used to implement the methods described above associated with predicting and quantifying free silicon in a geological formation. Hardware, firmware, software or a combination thereof may be used to perform the various steps and operations described herein.

Methods and systems in accordance with exemplary embodiments can be hardware embodiments, software embodiments or a combination of hardware and software embodiments. In one embodiment, the methods described herein are implemented as software. Suitable software embodiments include, but are not limited to, firmware, resident software and microcode. In addition, exemplary methods and systems can take the form of a computer program product accessible from a computer-usable or computer-readable medium providing program code for use by or in connection with a computer, logical processing unit or any instruction execution system. In one embodiment, a machine-readable or computer-readable medium contains a machine-executable or computer-executable code that when read by a machine or computer causes the machine or computer to perform a method for predicting and quantifying free silicon in a geological formation in accordance with exemplary embodiments and to the computer-executable code itself. The machine-readable or computer-readable code can be any type of code or language capable of being read and executed by the machine or computer and can be expressed in any suitable language or syntax known and available in the art including machine languages, assembler languages, higher level languages, object oriented languages and scripting languages.

As used herein, a computer-usable or computer-readable medium can be any apparatus that can contain, store, communicate, propagate, or transport the program for use by or in connection with the instruction execution system, apparatus, or device. Suitable computer-usable or computer readable mediums include, but are not limited to, electronic, magnetic, optical, electromagnetic, infrared, or semiconductor systems (or apparatuses or devices) or propagation mediums and include non-transitory computer-readable mediums. Suitable computer-readable mediums include, but are not limited to, a semiconductor or solid state memory, magnetic tape, a removable computer diskette, a random access memory (RAM), a read-only memory (ROM), a rigid magnetic disk and an optical disk. Suitable optical disks include, but are not limited to, a compact disk-read only memory (CD-ROM), a compact disk-read/write (CD-R/W) and DVD.

The disclosed exemplary embodiments provide a computing device, software and method for predicting and quantifying free silicon in a geological formation. It should be understood that this description is not intended to limit the invention. On the contrary, the exemplary embodiments are intended to cover alternatives, modifications and equivalents, which are included in the spirit and scope of the invention. Further, in the detailed description of the exemplary embodiments, numerous specific details are set forth in order to provide a comprehensive understanding of the invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein. The methods or flowcharts provided in the present application may be implemented in a computer program, software, or firmware tangibly embodied in a computer-readable storage medium for execution by a geophysics dedicated computer or a processor.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A method for predicting and quantifying free silicon in a geological formation, the method comprising:
generating free silicon data for a physical sample obtained from within the geological formation, the free silicon data comprising an identification of portions of the physical sample containing free silicon and a quantification of the free silicon contained in the portions of the physical sample containing free silicon;
generating a modified petro-elastic model for the geological formation comprising rock constituents that incorporates free silicon as one of the rock constituents and that quantitatively models how free silicon changes elastic properties within the geological formation; and
using the modified petro-elastic model to determine locations for wells in the geological formation.

2. The method of claim 1, wherein generating the free silicon data further comprises using scanning electron microscope-energy dispersive spectrometry on portions of the physical sample to generate the identification of portions of the physical sample containing free silicon.

3. The method of claim 2, wherein using scanning electron microscope-energy dispersive spectrometry comprises using at least one of leptonic beam scanning and baryonic beam scanning.

4. The method of claim 2, wherein using scanning electron microscope-energy dispersive spectrometry further comprises quantifying at least one of a ratio of silicon to aluminum, a ratio of zirconium to aluminum and an amount of molybdenum in each one of the portions of the physical sample.

5. The method of claim 2, wherein using scanning electron microscope-energy dispersive spectrometry further comprises identifying portions of the physical sample having an increase in a ratio of silicon to aluminum.

6. The method of claim 2, wherein generating the free silicon data further comprises using high magnification scanning electron microscopy on the portions of the physical sample containing free silicon to generate the quantification of the free silicon contained in the portions of the physical sample containing free silicon.

7. The method of claim 1, wherein the physical sample obtained from within the geological formation comprises at least one of a vertical borehole core and a horizontal borehole core.

8. The method of claim 7, wherein the portions of the physical sample comprise intervals along the vertical borehole core or horizontal borehole core corresponding to horizontal zones or vertical zones within the geological formation.

9. The method of claim 1, wherein generating a modified petro-elastic model comprises generating at least one of a modified mineral elastic properties model and a modified dry rock elastic properties model.

10. The method of claim 1, further comprising creating a three-dimensional model of the geological formation indicating volumes of free silicon throughout the geological formation using geophysical data obtained from the physical sample, seismic data covering the geological formation and the modified petro-elastic model.

11. The method of claim 10, wherein creating the three-dimensional model of the geological formation further comprises performing a petrophysical inversion using the modified petro-elastic model to create the three-dimensional model of the geological formation comprising an estimation of volumes of free silicon within the geological formation.

12. The method of claim 10, wherein creating the three-dimensional model of the geological formation further comprises at least one of performing an elastic stochastic inversion to generate a plurality of elastic models and performing a petrophysical stochastic inversion to generate a plurality of petrophysical models to determine an uncertainty in the volumes of free silicon in the three-dimensional model of the geological formation.

13. A computer-readable medium containing computer-executable code that when read by a computer causes the computer to perform a method for predicting and quantifying free silicon in a geological formation, the method comprising:
generating free silicon data for a physical sample obtained from within the geological formation, the free silicon data comprising an identification of portions of the physical sample containing free silicon and a quantification of the free silicon contained in the portions of the physical sample containing free silicon;
generating a modified petro-elastic model for the geological formation comprising rock constituents that incorporates free silicon as one of the rock constituents and that quantitatively models how free silicon changes elastic properties within the geological formation; and
using the modified petro-elastic model to determine locations for wells in the geological formation.

14. The computer-readable medium of claim 13, wherein generating the free silicon data further comprises using scanning electron microscope-energy dispersive spectrometry of the portions of the physical sample to generate the identification of portions of the physical sample containing free silicon.

15. The computer-readable medium of claim 14, wherein using scanning electron microscope-energy dispersive spectrometry further comprises identifying portions of the physical sample having an increase in a ratio of silicon to aluminum.

16. The computer-readable medium of claim 14, wherein generating the free silicon data further comprises using high magnification scanning electron microscopy on the portions of the physical sample containing free silicon to generate the quantification of the free silicon contained in the portions of the physical sample containing free silicon.

17. The computer-readable medium of claim 13, wherein generating a modified petro-elastic model comprises generating at least one of a modified mineral elastic properties model and a modified dry rock elastic properties model.

18. The computer-readable medium of claim 13, wherein:
the method further comprises creating a three-dimensional model of the geological formation indicating volumes of free silicon throughout the geological formation using geophysical data obtained from the physical sample, seismic data covering the geological formation and the modified petro-elastic model; and
creating the three-dimensional model of the geological formation further comprises performing a petrophysical inversion using the modified petro-elastic model to create the three-dimensional model of the geological formation comprising an estimation of volumes of free silicon within the geological formation.

19. The computer-readable medium of claim 13, wherein:
the method further comprises creating a three-dimensional model of the geological formation indicating volumes of free silicon throughout the geological formation using geophysical data obtained from the physical sample, seismic data covering the geological formation and the modified petro-elastic model; and
creating the three-dimensional model of the geological formation further comprises at least one of performing an elastic stochastic inversion to generate a plurality of elastic models and performing a petrophysical stochastic inversion to generate a plurality of petrophysical models to determine an uncertainty in the volumes of free silicon in the three-dimensional model of the geological formation.

20. A computing system for predicting and quantifying free silicon in a geological formation, the computing system comprising:
a storage device comprising geophysical data obtained from a physical sample obtained from within the geological formation and seismic data covering the geological formation; and
a processer in communication with the storage device and configured to:
generate free silicon data for the physical sample, the free silicon data comprising an identification of portions of the physical sample containing free silicon and a quantification of the free silicon contained in the portions of the physical sample containing free silicon;
generate a modified petro-elastic model for the geological formation comprising rock constituents that incorporates free silicon as one of the rock constituents and that quantitatively models how free silicon changes elastic properties within the geological formation; and
use the modified petro-elastic model to determine locations for wells in the geological formation.

* * * * *